DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED JULY 28, 1970

876 O.G. 816

T876,006
MEDICAMENT

Barry M. Brown, 1669 Lake Ave., Rochester, N.Y. 14650

Filed Jan. 22, 1970, Ser. No. 5,118
Int. Cl. A01n *17/00;* A61k *9/00;* B44d *1/02*
U.S. Cl. 424—35
No Drawing. 5 Pages Specification

An aldehyde-liberating pharmaceutical core such as hexamethylene-tetramine, or its derivatives such as hexamethylene tetramine mandelate (also known as methanamine mandelate), is coated with cellulose acetate phthalate (CAP) containing acetic acid or tartaric acid to preserve its enteric solubility properties. Acetic acid may be applied as a dilute 2% aqueous solution to the CAP followed by filtering and drying. Tartaric acid may be added to a solution of CAP in an organic solvent such as acetone, in an amount between 0.25 and 5% by weight of the CAP.